(12) United States Patent
Littrup et al.

(10) Patent No.: US 11,197,707 B2
(45) Date of Patent: *Dec. 14, 2021

(54) CRYOTHERAPY PROBE

(71) Applicant: ADAGIO MEDICAL, INC., Laguna Hills, CA (US)

(72) Inventors: Peter J. Littrup, Bloomfield Hills, MI (US); Alexei V. Babkin, Albuquerque, NM (US); Robert V. Duncan, Tijeras, NM (US); Pramod Kerkar, Bloomfield Hills, MI (US); Sergey T. Boldarev, Moscow (RU)

(73) Assignee: ADAGIO MEDICAL, INC., Laguna Hills, CA (US)

( * ) Notice: Subject to any disclaimer, the term of this patent is extended or adjusted under 35 U.S.C. 154(b) by 532 days.

This patent is subject to a terminal disclaimer.

(21) Appl. No.: 16/227,205

(22) Filed: Dec. 20, 2018

(65) Prior Publication Data
US 2019/0117288 A1    Apr. 25, 2019

Related U.S. Application Data

(63) Continuation of application No. 15/131,200, filed on Apr. 18, 2016, now Pat. No. 10,159,522, which is a continuation of application No. 14/087,947, filed on Nov. 22, 2013, now Pat. No. 9,408,656, which is a continuation of application No. 12/018,403, filed on Jan. 23, 2008, now Pat. No. 8,591,503, which is a continuation of application No. 10/757,768, filed on Jan. 14, 2004, now Pat. No. 7,410,484.

(60) Provisional application No. 60/440,541, filed on Jan. 15, 2003.

(51) Int. Cl.
*A61B 18/02* (2006.01)
*A61B 18/00* (2006.01)

(52) U.S. Cl.
CPC .......... *A61B 18/02* (2013.01); *A61B 18/0218* (2013.01); *A61B 2018/00529* (2013.01); *A61B 2018/00547* (2013.01); *A61B 2018/00577* (2013.01); *A61B 2018/0262* (2013.01)

(58) Field of Classification Search
CPC ................ A61B 18/02; A61B 18/0218; A61B 2018/0262
See application file for complete search history.

*Primary Examiner* — Daniel W Fowler
(74) *Attorney, Agent, or Firm* — Duane Morris LLP; Manita Rawat (57) ABSTRACT

A method of cooling a material including the steps of (i) providing a cryotherapy instrument, (ii) positioning a portion of the cryotherapy instrument adjacent the material to be cooled, and (iii) circulating a cryogenic fluid through the cryotherapy instrument under physical conditions near a critical point of a liquid-vapor system for the cryogenic fluid. The critical point defines a point in a phase diagram of the liquid-vapor system where molar volumes are substantially equivalent for liquid and gas, whereby vapor lock associated with cooling of the cryotherapy instrument is avoided.

12 Claims, 6 Drawing Sheets

CRYOTHERAPY PROBE

CROSS-REFERENCES TO RELATED APPLICATIONS

This is a continuation of U.S. application Ser. No. 12/018,403 entitled "Cryosurgical Probe", filed on Jan. 23, 2008, which is a continuation of U.S. application Ser. No. 10/757,768 (now U.S. Pat. No. 7,410,484), entitled "Cryosurgical Probe", filed on Jan. 14, 2004, which claims the benefit of U.S. Prov. Pat. Application No. 60/440,541 entitled "Cryosurgical Probe", filed on Jan. 15, 2003. The entire contents of each of the above-identified applications are incorporated herein by reference in their entirety for all purposes.

BACKGROUND OF THE INVENTION

This invention relates to generally to cryotherapy. More specifically, this application relates to image-guided control of cryoprobes and cryocoolers by a separate self-contained cryotherapy system.

Cryotherapy probes are used to treat a variety of diseases. The cryotherapy probes quickly freeze diseased body tissue, causing the tissue to die, after which it will be absorbed by the body or expelled by the body or sloughed off. Cryotherapy has traditionally been used within the operative setting to freeze liver and prostate tumors. Intraoperative ultrasound provided sufficient guidance for probe placement and progression of the ice front in relation to tumor margins. Cryotherapy for multiple outpatient treatments has a long history, due in part to its relatively painless delivery and ability to treat pain syndromes. The transition to outpatient cancer treatments requires rapidly freezing probes along with a convenient cryotherapy system. Without a relatively small, self-contained, easy-to-use cryosystem employing lower priced probes (i.e., currently each Endocare probe costs ~$400-1,500), the patient benefits of cryotherapy (i.e., lower pain, clear imaging of ablation zone and minimal scarring) will not adequately challenge the current popularity enjoyed by heat-based systems. For example, radiofrequency (RF) ablation has become the most common ablation modality perhaps more for its convenient set-up for physicians and lower disposable costs for hospital administrators than any distinct benefit over cryotherapy.

Percutaneous cryotherapy (PC) for breast, liver, kidney, bone and lung tumors has recently been described by Littrup, et al., copies of which are attached as Appendices A and B of U.S. Prov. Pat. Appl. Nos. 60/440,541 and 60/440,662, both of which have been incorporated by reference. PC monitoring is more difficult with standard ultrasound since it visualizes the treatment site from limited external positions. Therefore, CT and MRI have become the PC guidance modalities of choice due to their circumferential imaging and multi-slice rendering of a three dimensional volume. The phase change that occurs when tissue freezes (and resultant necrotic treatment margins) is much better seen by US, CT or MRI than the ablation margins of heat-based therapies. In addition, the necrotic treatment margin is much smoother and more predictable for ice than heat. When compared to heat-based ablation techniques, PC treatments are relatively painless and better preserve the underlying collagenous architecture of the ablated tissue. This produces better healing and less tissue disruption during, or after, the procedure. As long as bowel and major nerves are avoided, PC cancer treatments can be performed with safety of adjacent tissues via accurate treatment planning.

Adequate coverage of the tumor by ice, but with minimal side-effects, often requires several accurately placed cryoprobes. Multiple patents and applications have been published which attempt to address these issues. These cover cryoprobe design or freeze method [Cryomedical Sciences (U.S. Pat. Nos. 5,254,116 and 5,334,181); Endocare (U.S. Pat. Nos. 5,800,487 and 5,800,488); Cryogen (U.S. Pat. Nos. 5,910,104 and 6,475,212); Galil (U.S. Pat. Nos. 6,142,991 and 6,179,831)], computer controlled/interaction [Endocare (U.S. Pat. No. 6,139,544 and U.S. Pat. Publ. No. 2002/0016540A1); Cryogen (U.S. Pat. Nos. 5,513,742 and 6,471,694)] or MRI guidance [Galil (U.S. Pat. No. 5,978,697)]. Each of the foregoing patents and publications is incorporated herein by reference for all purposes. The Cryomedical Sciences efforts attempted to combat the flow difficulties encountered by liquid nitrogen ($LN_2$) in smaller probes (e.g., ≤3 mm) but required a highly complex system using large $LN_2$ volumes. While the Cryogen patents referred to a closed-loop gas system, no thermodynamic optimization was described to reduce engineering complexity. Therefore, companies with units which use large flow rates, or amounts of gas, to produce maximal freeze capacity per probe generally acknowledge the desire for an open system since the required compressors for such closed systems would become too large, expensive and unwieldy for portable use. In addition, the lack of optimized cryogenic design and probe configuration to produce the greatest freeze power for the minimal gas flow configuration prevents the design of smaller (i.e., <1.5 mm) probe diameters. While Galil has a 1.5 mm probe, its freeze capacity remains less than the Endocare 2.4 mm probe.

A combined effort is needed to optimize cryoprobes and the main driving system. A variety of cryotherapy instruments, variously referred to as cryoprobes, cryotherapy ablation devices, cryostats and cryocoolers, have become available. Currently preferred cryotherapy systems use Joule-Thomson (JT) cooling in devices known as JT cryostats. These devices take advantage of the fact that non-ideal gases, when rapidly expanded, become extremely cold. In these devices, a high pressure gas such as argon or nitrogen is expanded through a nozzle inside a small cylindrical sheath made of steel, and the JT expansion cools the steel sheath to sub-freezing cryogenic temperature very rapidly. An exemplary device is illustrated in U.S. Pat. No. 3,800,552, the entire disclosure of which is herein incorporated by reference for all purposes. This patent shows a basic Joule-Thomson probe with a sheath made of metal, a fin-tube helical gas supply line leading into a Joule-Thomson nozzle which directs expanding gas into the probe. Expanded gas is exhausted over the fin-tube helical gas supply line, and pre-cools incoming high pressure gas in what is known as a 'counterflow heat exchanger'. The counterflow heat exchanger is beneficial because by pre-cooling incoming gas with the outgoing gas flow the probe obtains lower temperatures.

U.S. Pat. No. 5,522,870, the entire disclosure of which is herein incorporated by reference for all purposes, applies the general concepts of Joule-Thomson devices to a device which is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is used to provide warming to a sufficiently high temperature. Furthermore, since the helium gas inversion temperature of approximately −240° C. is well below the base temperature of liquid nitrogen (−193° C.) helium is essentially an ideal gas at −240° C. and higher temperatures, and hence it does not cool during the gas expansion process. Various cryocoolers use mass flow warming, flushed backwards through the probe, to warm the probe after a cooling cycle [Lamb, Refrigerated Surgical Probe, U.S. Pat. No. 3,913,581; Longsworth, Cryoprobe, U.S. Pat. No. 5,452,582]. Each of these patents is also incorporated herein by reference for all purposes. A deficiency to broad adoption of gas-based systems by physicians and hospitals appears to be their lack of efficient self-contained systems.

Finally, cryotherapy needs to be considered as an adjuvant, or complementary, treatment with other cancer therapies. Successful reports from many papers on image-guided tumor ablation (including both heat-based and cryotherapy) were noted at the Radiological Society of North America's annual meeting for 2002 and 2003. Several prominent radiologists considered it to be "the fourth branch of oncology", in conjunction with surgery, radiation therapy and chemotherapy. Littrup, et al, have also noted the possible potentiation of cryotherapy, as well as reduced bleeding risk, by pre-injecting the region to be frozen with macro-aggregated albumin (MAA), hypertonic saline and epinephrine. This technique has been described by Dr. Order for treatment of pancreatic cancer with $P^{32}$, whereby the MAA creates an interstitial 'gel' effect and thus decreases subsequent fluid extravasation of the $P^{32}$ out of the tumor injection site (U.S. Pat. Nos. 5,538,726 and 5,424,288). In addition, injection of radiotherapeutic, or chemotherapeutic, agents directly into the tumor before or after the freeze may provide more thorough tumor ablation. Combining cryotherapy with radiation therapy, or chemotherapy, may reduce the overall risks of either chemotherapy or radiation therapy alone. Therefore, probe modifications which could deliver fluid through the probe, associated sheath system, or separate probe injection system would be of distinct benefit for future cryotherapy applications. In addition, probe modifications to allow minimal size with injection capacity would also benefit and re-invigorate the interest in PC for localized nerve ablation in pain management.

BRIEF SUMMARY OF THE INVENTION

Embodiments of the invention thus provide a cryotherapy probe that overcomes certain deficiencies of the prior art. In some embodiments, a gas-based cryotherapy probe is provided with a shaft having a closed distal end adapted for insertion into a body. A supply conduit is disposed longitudinally within the shaft for flowing gas towards the distal end, and a return conduit is disposed longitudinally within the shaft for flowing gas from the distal end. The gas is maintained at a lower pressure within the return conduit than in the supply conduit. A heat exchanger is disposed within the shaft in thermal communication with the supply conduit and return conduit to exchange heat from gas in the supply conduit to gas in the return conduit. A vacuum jacket is adapted to provide thermal isolation of the heat exchanger from the shaft.

The heat exchanger may comprise a plurality of strips of high-thermal-conductivity material in contact with the supply conduit and extending towards the return conduit. In some cases, the shaft comprises a nonmagnetic body and a metallic tip at the distal end of the shaft. In one embodiment, the shaft further has a plurality of injection ports for injection of fluids, such as may be used to enhance cytotoxicity and/or overall diameter of a lethal freeze. In other embodiments, electrical wiring is disposed within the vacuum jacket. For instance, such electrical wiring may comprise multifunction electrical wiring configured to permit multiple-point temperature monitoring of the distal end, to provide electrical stimulation of the body, including warming of the body, and the like. A Joule-Thomson port may be disposed in the distal end of the shaft and thermally coupled with the heat exchanger. In one embodiment, the heat exchanger comprises a plurality of strips of high-thermal-conductivity material in contact with the supply conduit and extending towards the return conduit.

Other embodiments of the invention provide a liquid-based cryotherapy probe with a shaft having a closed distal end adapted for insertion into a body and having a hollow zone within the shaft; such a hollow zone may provide for circulation and/or evaporation of liquid. A thermally isolated inlet capillary is provided in fluid communication with the hollow zone for providing a flow of liquid towards the hollow zone. An outlet capillary is provided in fluid communication with the hollow zone for providing a flow of liquid away from the hollow zone. A vacuum jacket is adapted to provide thermal insulation of the inlet and outlet capillaries within the shaft from the shaft. In one embodiment, the average cross-sectional area of the output capillary is greater than an average cross-sectional area of the input capillary. The shaft of the liquid-based cryotherapy probe may have injection ports and/or electrical wiring may be disposed within the vacuum jacket, as described above for the gas-based cryotherapy probe.

In other embodiments, a method is provided for cooling material. An end of a cryoprobe is positioned at the material to be cooled, or an inlet/outlet network is established within a region to be cooled. A cryogenic liquid is circulated through the cryoprobe or cooling network under physical conditions near a critical point of a liquid-vapor system for the cryogenic liquid. Vapor lock associated with freezing of the cryoprobe is thereby avoided. These embodiments permit the cryoprobe to have a high cooling capacity (e.g. >25 watts) yet have a diameter less than 2 mm. A cryoprobe with a diameter even less than 1 mm may be provided in one embodiment. In one specific embodiment, the cryogenic liquid is liquid nitrogen and the physical conditions comprise a pressure of about 33.5 atm. The material may comprise an imaging array, electronic circuits in a device, and the like. In some embodiments, the material may be electrically ablated by positioning a second cryoprobe in the material and forcing current to flow between electrically cryoprobe ends made of electrically insulating material.

Further embodiments of the invention provide a flow port. A structure defines an orifice through which material may flow. A high-yield-strength wire is disposed within the orifice and adapted to vibrate in response to a flow of material through the orifice. The orifice may be adapted to support high-Reynolds-number flow patterns. The flow port may form part of an engine fuel injector, part of a chemical spray nozzle, part of a fluid jet, and the like.

In one embodiment, a method is provided for determining a temperature within a body. A measurement current is supplied to a wire within the body. A forward voltage is measured while holding the measurement current substantially constant. A direction of the current is reversed by applying a negative of the measured forward voltage to the wire. A reverse voltage is measured while the direction of the current is reversed. A resistance of the wire is determined from the measured voltages to account for a thermal electromotive force differential associated with measurement leads in electrical communication with the wire. The temperature is determined from the determined resistance and a calibrated variation of resistance with temperature. The wire may be comprised by a cryotherapy probe having a shaft with a closed distal end adapted for insertion into the body, conduits for flowing cryogenic fluid within the shaft, and a post disposed within the closed distal end, the wire forming a plurality of turns about the post.

In another embodiment, a method of cooling a material is provided. The method includes (i) providing a cryotherapy instrument, (ii) positioning a portion of the cryotherapy instrument adjacent the material to cooled, and (iii) circulating a cryogenic fluid through the cryotherapy instrument under physical conditions near a critical point of a liquid-vapor system for the cryogenic fluid, wherein the critical point defines a point in a phase diagram of the liquid-vapor system where molar volumes are substantially equivalent for liquid and gas, whereby vapor lock associated with cooling of the cryotherapy instrument is avoided.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

1. Introduction: Thermodynamics of Cooling Cycles

As an initial matter, we analyze and compare two methods of cryogenic refrigeration that are currently being used in various cryotherapy tools: a) isoenthalpic expansion cooling (the Joule-Thomson process) from a high-pressure gas (Ar or $N_2$), and b) direct injection of a liquid coolant (liquid $N_2$, hereafter $LN_2$) into the tip of a cryoprobe.

a. Joule-Thomson (JT) Cooling

This refrigeration technique uses a high pressure gas supply (≈6,000 psi), a JT expansion jet that cools the tip of the probe, and a small heat exchanger that is mounted inside the cryoprobe. Assuming ideal (perfect) heat exchange between the gas streams, the maximum cooling power of the JT cooling is equal to 1.86 kJ/mol for Ar gas at its boiling temperature (and one atmosphere pressure) $T_{Ar}$=87 K. If nitrogen gas is used, the maximum cooling power is about 1.6 times less i.e. 1.15 kJ/mol.

The main disadvantage of this method is very large gas consumption since the vapor/liquid ratio after expansion is about 2.5. In practice this ratio is considerably larger since the heat exchange between the streams in a small probe is far from being ideal. This provides a limitation on the probe's diameter—in order to achieve a reasonable cooling power, the geometrical impedances of the gas channels in the probe should be sufficient to allow for the adequate amount of gas to be supplied to/from the JT junction.

b. Cooling with Liquid Nitrogen

A direct injection of the liquid coolant into a freeze zone of the cryoprobe appears to be much more effective when compared to JT cooling. For example, to achieve the same cooling power as in the JT process the required molar flow of the liquid coolant can be 3-4 times less (3.5 times for Ar and 4.5 times for $N_2$). Liquid nitrogen is the most commonly used and cheapest cryogenic liquid, and its boiling temperature is about 10 K lower under one atmosphere of pressure than that of argon. Thus, the analysis presented below is for $LN_2$.

$LN_2$ encounters vapor lock when standard pressures (1 atm) are considered since the volume expansion from liquid to gas is 171 fold (see molar volume in Table 1 below). The flow of $LN_2$ is thus rapidly blocked, and the flow of the very low density vapor phase at one atmosphere has very poor cooling power, eliminating the potential benefits of $LN_2$ cooling and its low costs. Considering the high pressures for the JT effect and our optimized flow considerations, it then follows that $LN_2$ may also be pressurized to eliminate flow disruption due to marked volume expansion. As the pressure is increased toward the critical point the vapor density increases, greatly reducing the negative impact to the refrigeration system when vapor forms. The critical point for $LN_2$ is reached at ~33.5 atm (Table 1) where the molar volumes are substantially equivalent for liquid and gas. While the fluid temperature has increase from 77K to ~130K (Table 1), a post compression heat exchanger may be used to cool the compressed $LN_2$ to the ambient bath temperature of 77K again. A typical phase diagram for a liquid like $LN_2$ can be seen in FIG. 1, whereby the critical point is noted, along with the projected compression sequence to a cooler operating point. Compression is first used to increase the pressure of $LN_2$ along the liquid-vapor curve; then, the heat exchange with the $LN_2$ bath lowers the compressed liquid temperature to the probe operating point as shown. We use the term 'near critical nitrogen' to refer to liquid nitrogen held near its critical pressure of 33.5 atmospheres.

The only complication to the technical design in this case is the need to thermally isolate the inlet (coolant supply) tube so that the compressed $LN_2$ will arrive at the cryoprobe at a temperature close to 77 K. It is also desirable that the liquid flow not form gaseous bubbles anywhere except possibly at the probe tip under large heat loads, so as not to create a vapor lock condition that limits the cooling power. By operating near the critical point of the liquid—vapor system the vapor phase is much more dense than it would be if operated near atmospheric pressures. This makes the volume expansion of the liquid into the vapor phase much less, and it makes the resulting vapor phase a much more effective coolant.

The design of the $LN_2$ circulation cryoprobe itself becomes significantly simpler in comparison to that of the JT cycle based cryoprobe—both the internal heat exchanger and the JT jet are no longer required. The overall internal structure of the probe can be reduced to a very simple design discussed below in connection with FIG. 5. This simplified design results in lower manufacturing costs for the probe, which is important in markets where the probe is disposed of after each use, or returned for a re-cycling credit. The optimal performance of the probe and its main characteristics can be estimated based on the thermodynamic properties of nitrogen, which are summarized in the Table 1 below.

TABLE 1

Thermodynamic Properties of $LN_2$
Properties of $LN_2$ along liquid/gas equilibrium

| | | Molar Enthalpy | | Molar Volume | | | |
|---|---|---|---|---|---|---|---|
| P (atm) | T (K) | $I_L$ (J/mol) | $I_G$ (J/mol) | $V_L$ (cm³/mol) | $V_G$ (cm³/mol) | Latent Heat L (J/mol) | $Q_{MAX}$ (J/mol) |
| 1 | 77.36 | 3550 | 9100 | 35 | 6000 | 5560 | 5560 |
| 2 | 84 | 3900 | 9150 | 37 | 3200 | 5250 | 5600 |
| 3 | 88 | 4200 | 9250 | 38 | 2300 | 5050 | 5700 |
| 5 | 94 | 4500 | 9350 | 39 | 1600 | 4850 | 5800 |
| 7 | 99 | 4750 | 9400 | 40 | 1000 | 4650 | 5850 |
| 10 | 104 | 5100 | 9450 | 42 | 750 | 4350 | 5900 |
| 15 | 111 | 5500 | 9400 | 45 | 450 | 3990 | 5850 |
| 20 | 116 | 6000 | 9250 | 48 | 320 | 3250 | 5700 |
| 25 | 120 | 6450 | 9100 | 53 | 240 | 2550 | 5500 |
| 30 | 124 | 6950 | 8750 | 69 | 165 | 1850 | 5200 |
| Critical point | | | | | | | |
| 33.5 | 126.15 | 7950 | | 90 | | 0 | 4400 |
| Overcritical Nitrogen | | | | | | | |
| 35 | 130 | 8850 | | 115 | | — | 5000 |

The last column of the table $Q_{MAX}$ is the maximum value of the cooling power that can be achieved in this process assuming that nitrogen is "overcooled" through heat exchange with the ambient $LN_2$ bath at 77.4 K. As we see, under these conditions the cooling power is almost independent of pressure up to approximately 30 bars. Moreover, almost the same level of refrigeration per unit mass flow can be produced in the supercritical regime at the pressure ≈35 bar (bottom line in the Table 1). After initially establishing flow with overcritical nitrogen, the $Q_{MAX}$ can still be increased by 18% (5,900/5,000 J/mol) by dropping the operating pressure to 10-15 atm. Operating at this level still represents a 6% increase in $Q_{MAX}$ (5,900/5,560) over trying to use $LN_2$ at 1 atm, even if vapor lock could somehow be avoided at this pressure.

It is worth noting that "classical" evaporating cooling (where the cooling effect is due to the latent heat only) is able to provide a comparable cooling power only in the low pressure limit. However, running the cryoprobe in the low pressure regime is difficult because of possible vapor locking. It is much more desirable to design a probe that cools by liquid flow, with little or no evaporation at the cooling tip. By avoiding the huge volume expansion into the vapor phase within the conventional $LN_2$ cooled probe (when the $LN_2$ pressure is near ambient pressure of one atmosphere) it is possible to use a much smaller diameter return flow line from the tip, permitting the overall probe diameter to be reduced greatly without sacrificing freeze power. Under very large heat loads, evaporation will occur at the probe tip, but this will have little adverse consequence on the probe freeze power if the liquid nitrogen pressure is close to the critical pressure. Near the critical pressure the vapor phase density is almost the same as in the liquid phase, reducing adverse effects on the probe freezing power when the vapor phase forms. This is one advantage of operating near the critical pressure. In order to achieve the required cooling power, the flow of the $LN_2$ coolant through the cryoprobe has to be maintained on a reasonably high level. This imposes a restriction on the geometrical sizes of the cryoprobe; an estimation of the flow dynamics follows in the next section.

c. Flow Dynamics

In the following estimates it is assumed that the desired cooling power of the probe is 25 W. From Table 1 we find that in an evaporative $LN_2$ refrigerator this cooling power corresponds to a flow rate 0.005 mol/s. This value is used in the calculations below.

Regrettably, the available nitrogen viscosity data is incomplete. The known values are summarized in the Table 2 below:

TABLE 2

Viscosity of gaseous and liquid nitrogen at different temperatures

| T | Viscosity, $10^{-6}$ (Pa · s) | | |
|---|---|---|---|
| (K) | Gas at 1 atm | Gas at 25 atm | Liquid $N_2$ |
| 80 | 5.4 | 130 | ≈150 |
| 90 | 6.3 | 91 | 110 |
| 100 | 7.0 | 72.8 | 90 |
| 110 | 7.4 | 55.6 | 65 |
| 120 | 8.3 | 38.5 | — |
| 130 | 8.9 | 10.6 | — |

(i) Reynolds Numbers

The corresponding Reynolds numbers (R) can be estimated using the following equation:

$$R = \frac{\rho v d}{\eta} = \frac{4\rho \dot{V}}{\pi \eta d} = \frac{4}{\pi} \frac{\dot{m}}{\eta d}$$

where ρ is the density, v is the flow velocity, V is the corresponding volumetric flow rate, and m=ρV is the mass flow rate. Numerically, assuming the flow rate of 0.005 mol/s and d=0.5 mm, we obtain:

$$R = \frac{4}{\pi}\frac{28\cdot 10^{-3}\cdot 5\cdot 10^{-3}}{5\cdot 10^{-4}\eta} = \frac{0.356}{\eta[Pa\cdot s]}$$

(ii) Pressure Drop
1. Case of the Liquid Flow

Assuming initially that in liquid $\eta=10^{-4}$ Pa·s (some average value) we obtain that for a 0.5 mm capillary the Reynolds number has to be on the order of 3,500 (1,800 for a 1 mm capillary or 6,000 for a 0.3 mm one). This indicates that the flow is in the transition zone (laminar to turbulent) and in this case the Colebrook equation of an ideally smooth circular pipe is used to estimate the pressure drop $\Delta p$. The resistance coefficient K in this formula can be estimated as $K=fl/d\approx 20$, where $f=4\cdot 10^{-2}$ is the friction factor, $l=25$ cm is the length of the capillary and $d=0.5$ mm is its inner diameter. Then the pressure drop $\Delta p$ can be defined as $$\Delta p = K\frac{\rho v^2}{2}$$

taking into consideration that $$\rho v = \frac{4}{\pi d^2}\dot m$$

we finally obtain $$\Delta p = K\frac{8}{\pi^2 d^4}\dot m \dot V$$

The average molar volume of the liquid is $v_L\approx 40$ cm³/mol. This multiplied by our optimal circulation rate of 0.005 mol/s results in $\dot V\approx 0.2$ cm³/s. Finally, from the above equation and with $d=0.5$ mm, we obtain $\Delta p_{0.5}\approx 7{,}260$ Pa. Similarly, for $d=0.3$ mm we obtain $f=0.037$, $K=30.8$, and $\Delta p_{0.3}=8.7\cdot 10^4$ Pa. Hence at 0.3 mm we suffer a pressure drop of about 87% of an atmosphere, which is manageable in the engineered support system.

The probability of the vapor lock for this flow can be estimated using so called Weber number that is the ratio of the kinetic energy of the flow to the characteristic surface tension energy. The average velocity of the liquid is given by $v=4\dot V/\pi d^2\approx 1$ m/s for a 0.5 mm capillary. Surface tension of the liquid nitrogen at 90 K (average) is equal to $\sigma=6\cdot 10^{-3}$ N/m. Hence the Weber number becomes $W_{0.5}=\rho v^2 d/\sigma\approx 600$ indicative of a very low probability of a vapor lock. Correspondingly, $W_{0.3}=270$.

2. Case of the Gaseous Return Flow

Assuming the circulation rate $5\cdot 10^{-3}$ mol/s, the volumetric flow rate and the corresponding flow velocity for saturated $N_2$ vapor in the 0.5 mm ID capillary are calculated and presented in the Table 3 below:

TABLE 3

| Volumetric flow rate and flow velocity | | | | | | | | | | |
|---|---|---|---|---|---|---|---|---|---|---|
| P (atm) | 1 | 2 | 3 | 5 | 7 | 10 | 15 | 20 | 25 | 30 |
| $\dot V$ (cm³/s) | 30 | 16 | 11.5 | 8.0 | 5.0 | 3.8 | 2.2 | 1.6 | 1.2 | 0.82 |
| $v$ (m/s) | 153 | 81.5 | 58.6 | 40.7 | 25.5 | 19.4 | 11.2 | 8.2 | 6.1 | 4.2 |

Note that the flow velocities at the low pressure end appear to be very close to the sound velocity in nitrogen at these temperatures—at 77K the speed of sound is 180 m/s and it slightly raises with temperature reaching 200 m/s at 100K.

Thus, the applicability of the incompressible liquid approximation used in our analysis is restricted to the region of relatively high pressures (in practice >5 bars).

The Reynolds numbers can be estimated using the equation in the previous subsection, although we need to interpolate the viscosity data. That gives the following estimates for a 0.5 mm capillary: $R_{1\text{-}2\ bar}\approx 6\cdot 10^4$, $R_{3\text{-}5\ bar}\approx 5\cdot 10^4$, $R_{15\text{-}25\ bar}\approx 1\cdot 10^4$. An estimation for the pressure drop is more difficult than in the case of liquid flow and is done in the limit of an incompressible gas. Then, taking $R=5\cdot 10^4$, $f=0.021$, and the friction coefficient $K=fl/d\approx 10$, we obtain $\Delta p\approx 2.2\cdot 10^5$ Pa, which is about 2.2 atmospheres. Again, the pressure is manageable with embodiments of the invention described herein.

(iii) Volume of $LN_2$ Required

The problems with prior high volumes of $LN_2$ usage in the other cryosystems have also been overcome. Namely, such units would use up the 50 liters of supercooled $LN_2$ within a "slush" dewar well before even a single large case was over. This required a time consuming "regeneration" cycle of re-cooling the $LN_2$ within the return dewar to re-supply the slush dewar. Such systems pressurized $LN_2$ to only 5 atmospheres, which was not adequate to obtain the near critical properties discussed above. Then the compressed $LN_2$ was supercooled to about 63 K through heat exchange to a $LN_2$ bath in a 'slush dewar' that was held at a vacuum of about 98 torr to reach the triple point on the liquid nitrogen phase diagram. This supercooling of the $LN_2$ at 5 atmospheres to the temperature of the slush dewar provided only small additional cooling power than would be obtained if the compressed liquid nitrogen had been cooled to 77K through heat exchange with a liquid nitrogen bath at one atmosphere. Hence the engineering complexity of the slush dewar did not justify the very minimal improvement in cooling capacity of their liquid nitrogen flow following heat exchange with the slush dewar. As displayed in Table 1, liquid nitrogen at 25 atmospheres has essentially the same cooling power, Qmax, as does liquid nitrogen at its one atmosphere boiling point, but at 25 bar the vapor phase density is more than one fifth of the liquid density, and over thirty times more dense than the vapor phase under one atmosphere of pressure. Hence flowing liquid nitrogen at 25 bar will provide the full advantages of liquid nitrogen flow cooling at lower pressures without the adverse effects of cooling system failure due to vapor lock at the lower pressures.

In the prototype small probe tested within this application we found that 0.02 STP liter per second of nitrogen was required to produce full cooling power. This flow rate corresponds to one liquid liter per hour of $LN_2$ under its 'ambient' conditions (at its boiling point under one atmosphere of pressure). This liquid must be compressed to pressures near its critical point, and the heat of compression from one atmosphere to this pressure must be taken away by evaporation of the surrounding liquid nitrogen bath which cools the compressed $LN_2$ back to 77 K following its compression to 30 atmospheres. This removal of the heat of compression to 30 bar corresponds to an additional evaporation of 0.81 liters per hour of $LN_2$ under ambient conditions, as discussed below.

In summary, 36 W of additional cooling are required to remove an assumed heat of compression from the 0.2 standard liters per second (SLPS @ 1 atm.) flow rate per probe. This means that each probe will require 0.8 liters of $LN_2$ per hour to remove the heat of compression. This adds to the direct probe consumption of one liter per hour to give a total system $LN_2$ consumption of 1.8 liter per hour per probe of $LN_2$ for this fully self-contained system configuration running full-out. At lower flow rates the consumption will be much less, but we have therefore assumed ~2 liters of $LN_2$ per probe per hour as the absolute worst case estimate.

TABLE 4

Physical properties of $LN_2$
From Jacobsen and Stewart, $N_2$ tables
J. Phys. Chem. Ref. Data 2, 757 (1973)

|  | mol/l | g/cm3 | T (K) | S (J/mol/K) | H (J/mole) |
|---|---|---|---|---|---|
| density at SVP and 77 K | 28.865 | 0.808607 | 77.347 | 79.53 | −3401.75 |
| density at SVP = 30.574 bar | 16.388 | 0.459084 | 124 |  | −13.85 |
| density at 30 bar and 78 K | 28.998 | 0.812333 | 78 | 79.45 | −3307.3 |

| Once at 30 bar and 78 K: | 56.82 | Cp (J/mol/K) |
|---|---|---|
| Heat of Compression = | T ΔS = 6.24 | J/mol |
| Compression factor = | 1.004608 |  |
| Heat of compression = | 6.24 | J/mol |
|  | 180.9475 | J/l |
|  | 36.1895 | W/(0.2 l/s) |
| Latent Heat (77 K/1 atm) = | 199 | J/g |
|  | 160.9128 | J/cm³ |
| So, 36 W boils | 0.224901 | cm³/s |
|  | 809.6451 | cm³/hr = 0.81 l/hr | d. Comparison

For a small diameter cryoprobe it may be more advantageous to use $LN_2$ in the freeze zone as compared to the JT-cooling cycle—the flow rate required to provide the same cooling power is much less. This is especially true since the flow velocities in the gas phase appear to be already very close to the sound velocity in the return line assuming a JT process. This problem is alleviated by using liquid nitrogen.

A temperature of the compressed liquid nitrogen has to be supercooled close to its boiling temperature under one atmosphere (77K); in this case the increase in working pressure does not result in a decrease of cooling power up to the pressures almost as high as the critical pressure, as displayed in Table 1.

For a designed cooling power 25 W (or flow rate 5 mmol/s) the acceptable diameters of the inlet/outlet capillaries can be estimated assuming reasonable pressure difference on its ends and the flow velocities. To deliver this cooling power in practice the inlet capillary may be larger than about 0.3 mm (ID) and the outlet capillary may be larger than about 0.5 mm (ID). Thus the outer diameter of the vacuum jacketed cryoprobe may be made as small as about 1.2 mm. For a JT-based probe the probe is generally at least 2.5 mm in diameter to provide a comparable cooling power. As described earlier, this greater diameter in the JT probe is used to support the counterflow heat exchanger without exceeding the speed of sound in the return gas flow line.

A very small diameter cryoprobe can be built if supercritical, or near critical, nitrogen is used in its cooling cycle. This may involve working at 29-35 bars of pressure and temperatures 78-80K. The cooling power for this cycle rises with temperature and for 0.005 mol/s flow rate reaches 25 W at 130K.

2. Cryotherapy Probe a. Overview

This disclosure details several self-contained cryotherapy probe designs for both liquid and gas-based systems, where "self-contained" is intended to refer to open or closed-loop configurations that permit sustained use without repeated refilling or exchange of tanks. The optimal physics-based probe and system configurations are described for various embodiments which address the prior problem of vapor-locking with liquid based systems and optimized flow considerations to allow more efficient and/or closed-loop gas-based systems.

Methods, cryoprobe device(s), and cryotherapy systems for delivering percutaneous cryosurgery and cryotherapy that overcome deficiencies of the prior art are now described. The process can either use a number of small isenthalpic cooling probes which have greater freeze capacity per unit size (and gas flow rate), or may utilize a new form of delivery of liquid cryogens (i.e., $LN_2$) that avoids vapor-lock by compressing the liquid to its near-critical point. These probes may clinically achieve increased freeze capacity without increasing engineering complexity or cost, yet allowing significant operator-interactive control as desired. The cryoprobe design may achieve increased thermodynamic and/or hydrodynamic efficiency so that the reduced size and cost of the engineered system are achieved in an associated closed-cycle system for gas-based systems, or a self-contained system for the delivery of near-critical fluids. A closed-cycle system design for gases, or an efficient near-critical liquid system, reduces the operational complexity by being fully self-contained, so compressed gas tank changes or lengthy regenerative/re-filling cycles are not required during extended medical procedures. Once multiple probes are inserted their position within the intended freeze zone is determined using an imaging modality, such as CT, MRI or ultrasound. The flow of the closed-cycle gas through each of the multiple probes is adjusted automatically to sculpt the freeze zone to match the intended freeze region specified by the physician. The probe construction has thus been matched to programmable, interactive, self-contained system operation. A new thermocouple design allows probe tip measurement in even smaller probes (i.e., <2 mm), can facilitate probe heating for thawing, simplifies construction and lowers manufacturing costs. The injection ports of the cryoprobe(s), or separate multiprong injection probe system, also allows modulation of the freeze parameters, or extent of freeze, within the adjacent tissues.

As illustrated above, the principles of vapor lock effectively limit the cooling capacity of conventional flow liquid-nitrogen systems. For example, U.S. Pat. Nos. 5,254,116 and 5,334,181 described an approach that increased cooling rates of probes to less than a minute and allowed probe temperatures around −200° C., which was lower than the boiling temperature of $LN_2$ under ambient conditions (−197° C.). However, this required a complex system that sub-cooled $LN_2$ to ~−200-208° C. via two large dewars that supplied and recycled the $LN_2$, one of which (the 'slush dewar') had to be maintained at a reduced pressure of approximately 100 torr. The probe design allowed $N_2$ gas to escape via tiny holes from the supply line to the return line to allow continuous flow of $LN_2$, even during the ~170-fold gaseous expansion of LN$_2$ within the probe tip that caused evaporative cooling of the biological tissues adjacent to the conductive metal of the probe tip. In addition to minimizing vapor-lock, the concentric position of the supply line inside the return line also allowed some escaping LN$_2$ to create cooling of the returning LN$_2$ for capture in the receptacle dewar. However, this system was quite large for most operating rooms, let alone more crowded imaging suites (e.g., CT), and wasn't efficient in operating procedures or LN$_2$ consumption. The sub-cooling process took additional preparation time after the machine was set-up and the high volume flow frequently emptied the "slush" dewar during large cases, requiring another time-consuming "regenerative" cycle to re-fill the slush dewar. The time of nearly a minute for each probe to be frozen stuck and several minutes to thaw to become free from the surrounding tissue, so that the probe may be moved, made the system more frustrating for time-conscious operating room or imaging suites.

The embodiments described herein provide for improvements in thermodynamic and hydrodynamic efficiencies for gas-based probes and allows better consideration of future closed-cycle systems using mixed gases. Our observation of properties of the transition of compressed gas to the liquid state, at and beyond the JT port of the expansion chamber, also suggested certain concepts incorporated in some embodiments for avoiding flow problems with liquid nitrogen as it expanded to a gaseous state within the expansion chamber of the tip.

Prior liquid nitrogen based (LN$_2$) probe cooling systems operated near or slightly above atmospheric pressure, where the liquid is 170 times more dense than its vapor at the same temperature. This is far from ideal, since if heat absorbed by the flowing LN$_2$ cryogen exceeds a threshold level, then the vapor phase of LN$_2$ will form in an uncontrollable way within the liquid flow and this vapor phase will displace suddenly a much larger volume, equal to this same factor of 170 times the volume of the liquid evaporated (see Section 1 above). This fills the probe tubing with a large quantity of gas that is far less efficient at removing heat from the surrounding tissue through the probe wall. The excess heat from the tissue around the probe that now can not be carried away by circulating liquid causes more and more evaporation of the LN$_2$ in the probe until the entire probe is filled with vapor. This vapor lock is a significant limitation to the reliable operation of LN$_2$ systems at low pressure. Similar vapor lock problems have been a significant limitation to the use of LN$_2$ flow cooling to support long-wavelength infrared sensors on the image planes of systems on satellites, aircraft, and other remote platforms for imaging various objects of interest, and a significant limitation in cooling many other devices by LN$_2$ circulation.

The threshold heating power ($Q_{MAX}$ in Table 1 times the molar flow rate) to create the vapor phase in the probe depends on both the rate of LN$_2$ flow through the probe, and the pressure of the LN$_2$ within the flow. If L is the latent heat per unit volume of the LN$_2$, and H is the amount of heat energy necessary to warm the LN$_2$ to the temperature where vapor may form, then this threshold heating power level to create vapor in the probe, in watts, is simply (L+H) dV/dt, where dV/dt is the volume flow rate of LN$_2$ through the probe.

As discussed by many authors [see, for example H. Eugene Stanley, Introduction to Phase Transitions and Critical Phenomena (Oxford University Press, 1971)], as the pressure is increased the difference in the densities between the liquid and vapor phases becomes less and less, until at the critical point pressure and temperature the liquid and vapor have the exact same density. Hence, as the pressure of the circulating LN$_2$ cryogen is increased, the consequence of vapor formation on the proper operation of the probe becomes far less significant, since the volume expansion of the vapor phase beyond the original liquid volume evaporated becomes less as the pressure is increased, until it becomes zero at the critical point. Furthermore, the much higher density of the vapor phase near the critical point makes it far more efficient at circulation cooling than the vapor phase far from the critical point. Hence if the LN$_2$ is circulated at exactly its critical point pressure and temperature, then the catastrophic failure of probe freezing associated with vapor lock, which occurs at lower working pressures, physically can not occur. This results in a vastly more reliable and hence easier to use cryogenic freeze cycle.

As discussed in Section 1 above, the Weber Number, which is the ratio of the kinetic energy of flow to the surface energy of the liquid—vapor interface, is a good indicator of the likelihood of vapor lock. When the Weber number is large, then the likelihood of vapor formation is small. Hence it is possible to design the circulation system to operate away from the critical point conditions, where vapor lock is impossible, to lower pressures where vapor formation is very improbable, provided that the Weber number is sufficiently large. This implies that the optimal control cycle for the LN$_2$ flow system may start at high pressure (critical or near-critical conditions) and then relax to lower pressures as the LN$_2$ flow is well established, provided that the Weber Number remains large. At a given sub-critical operating pressure the Weber Number may be increased by increasing the flow, however this option is less desirable because the increased flow expends the LN$_2$ more rapidly, resulting in more frequent refills and hence in a more complex engineered system to cool the cryoprobe. As discussed above, near the critical point two-phase flow remains efficient in cooling applications, since the vapor density is large. This higher pressure operation, near the critical pressure, makes the consequence of vapor formation much less detrimental to the proper freeze power of the probe.

Once the liquid has been compressed to elevated pressures near its critical pressure it may be passed through a heat exchanger with the ambient pressure LN$_2$ bath in order to over-cool the compressed liquid, resulting in a greater cooling power per unit volume of the flowing cryogen, as discussed in Section 1 above.

Embodiments of the invention provide a novel method of circulating LN$_2$ cooling with the LN$_2$ held near its critical point to avoid vapor lock (see discussion of FIGS. 5-7 below). This method of cooling, called Near Critical Nitrogen (NCN) cooling, is applied below to the optimization of the freeze performance of very small probes (see discussion of FIG. 5 below), where more conventional cooling techniques based on the JT process become impractical, as discussed in Section 1 above. Hence this NCN cooling process makes it possible to reduce the diameter of cylindrical freeze probes to less than 1.5 mm, and to vastly reduce the complexity and size of the engineered system into a single, self-contained unit with no external pressure tanks (see discussion of FIG. 6 below).

While this improved method of cooling is described herein for application to probes for cryosurgery (see discussion of FIG. 7 below), it has very broad applicability to all cryogenic cooling applications involving a flow of liquid cryogen. More generally, the methods described herein may be used to cool other devices with any cryogen flow operating near its critical point. These devices may include sensors within image plane arrays for remote sensing applications, superconducting wires and cables, and all other devices requiring cryogenic support. Other cryogens of interest using this technique include and liquefied gas, including argon, neon, xenon, helium, hydrogen, and oxygen, to name a few. These are single component flowing liquid-vapor systems. Mixtures of substances in flowing liquid vapor systems may also be used in this way, such as flowing hydrocarbon gas mixtures, provided that their critical point pressures and temperatures are readily obtained within the engineered cooling or liquid-gas processing system.

In addition, certain prior-art cryoprobe design is limited by not actually placing thermocouples within the active cryogen chamber within the tip of the cryoprobes themselves in order to avoid manufacturing complexity, etc. For both prior $LN_2$ and prior gas-based systems, thermocouples are more generally placed in or near the return line such that the thermocouple read-outs are not the actual, lowest tip temperature. For example, assuming perfect heat transfer from the JT expansion chamber, tip temperatures for Argon should be close to its boiling point of 87K (or ~−183° C.). However, even the most recently available probes rarely display probe temperatures below −150° C. If conventional cryoprobes could be miniaturized to even smaller dimensions (i.e., <2 mm), specialized engineering efforts to place the thermocouples at the tip would increase the price of the cryoprobe beyond their already costly levels (~$500-1500). The thermal anchoring of small thermocouples is an additional concern, since these typical copper-constantan thermocouples would need to be mounted within the vacuum space of the shaft but thermally anchored to the cryogenic tip of the probe. Alternatively, the thermocouple may be placed in the flow channel directly; however, this may require a hermetic feed-through for the wires, driving up cost. In new small probe designs this would require that the thermocouple be no larger than about 100 microns along its largest dimension, placing a demanding and expensive limitation on the cryoprobe assembly technique. The embodiments of the invention discussed herein permit accurate, rapid resistance thermometry in very small cryoprobe tips, as well as in adjacent probes, while reducing costs well below current thermocouple measurement systems ($35-124) used in cryoprobes today. The use of resistance thermometry is highlighted here to demonstrate its remarkable flexibility in allowing very small probe design, multiple functions (i.e., thermometry, nerve stimulation and probe heating) and yet reducing production costs for an otherwise disposable cryoprobe.

b. Cryoprobe Designs

Figure 2:
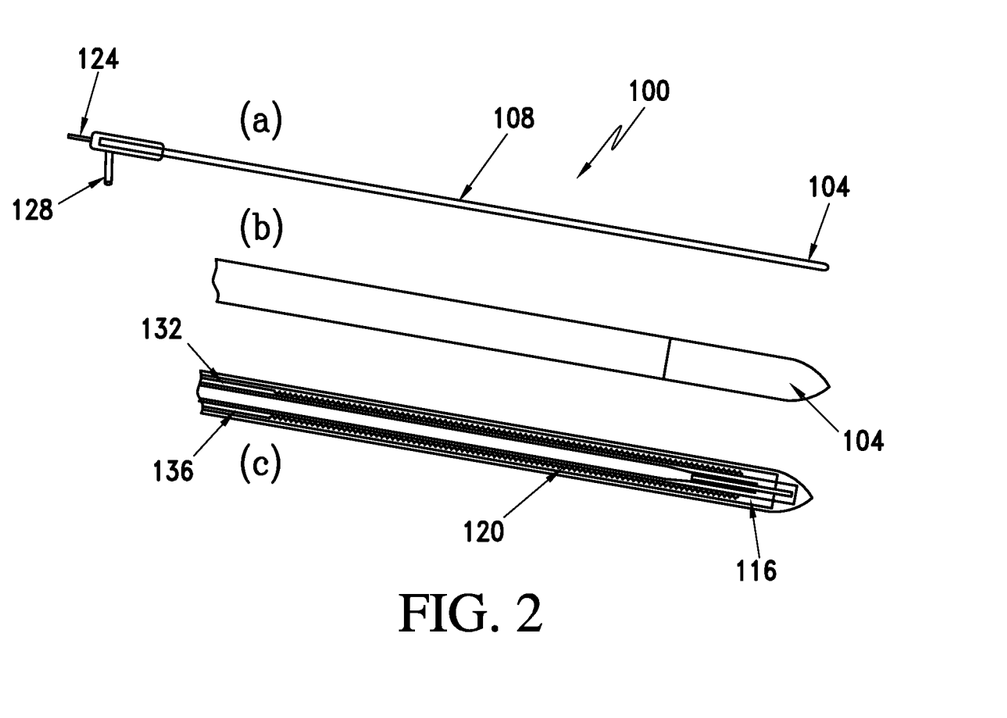
FIG. 2 is a schematic illustration of an embodiment of a gas-based cryoprobe in accordance with an embodiment of the invention.

A structure for a cryoprobe according to an embodiment of the invention is provided in FIG. 2. Part (a) of FIG. 2 provides a perspective view of the cryoprobe 100, which includes a shaft 108 having a metal tip 104. In one embodiment, the metal tip comprises a copper tip with gold plating. Gas is flowed through the cryoprobe 100 through a high-pressure inlet 124 and returns from a low-pressure outlet 128. Part (b) provides an expanded view of a distal end of the cryoprobe showing the metal tip 104 more clearly. A cutaway view of the tip is shown in part (c) of FIG. 2, illustrating a supply conduit 136 that is provided in fluid communication with the high-pressure inlet 124 and a return conduit 132 that is provided in fluid communication with the low-pressure outlet 128. A heat exchanger 120 acts precools the incoming high-pressure gas along the supply conduit 136 with the outgoing gas flowing along the return conduit 132, allowing lower temperatures to be obtained. A Joule-Thomson junction 116 is provided in fluid communication with the heat exchanger. As discussed further below, the shaft 108 may be vacuum jacketed from the inner heat exchanger 120 to ensure that the shaft 108 remains at ambient temperature.

Figure 3:
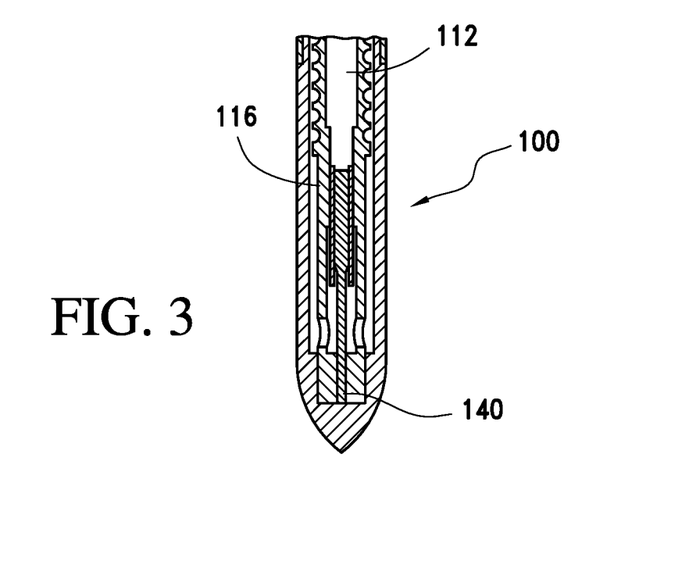
FIG. 3 is a schematic illustration of a JT port with a hard wire made of material such as hardened steel or niobium-titanium alloy, extending ~5 mm within the capillary inlet supply tube.

A more detailed view of the Joule-Thomson junction is evident from FIG. 3, which provides an expanded view of the cutaway schematic of FIG. 2(c). The Joule-Thomson junction comprises a high-yield strength wire 140 extending within the capillary source conduit 136. The high-yield strength wire 140 may comprise, for example, a steel or niobium-titanium alloy wire, among other high-yield strength materials.

Figure 4:
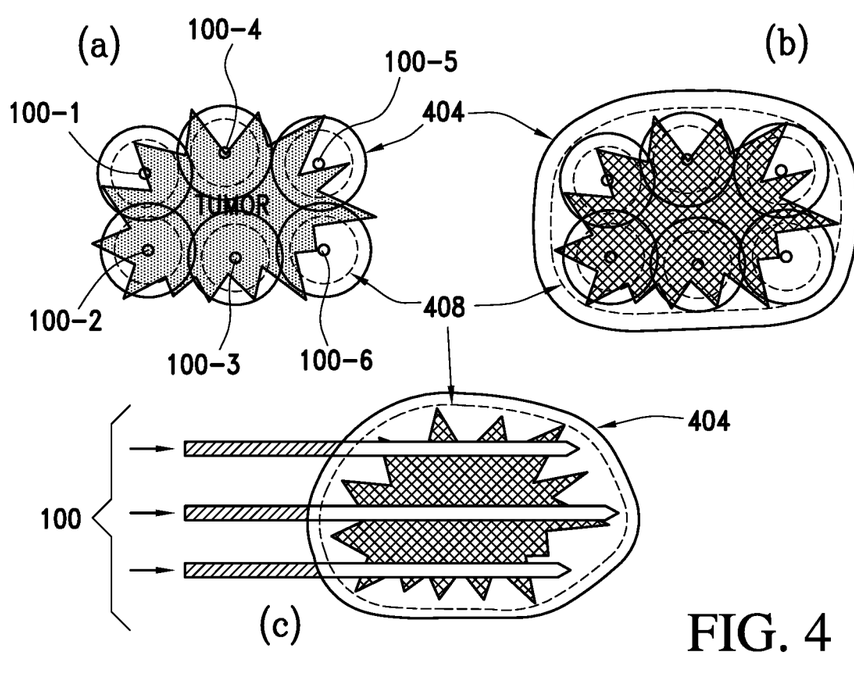
FIG. 4 is a schematic illustration of a tumor treatment using six cryoprobes in accordance with an embodiment of the invention.

FIG. 4 provides a schematic illustration of a tumor treatment that uses six cryoprobes 100 in accordance with an embodiment of the invention. The probes 100 are separately driven and computer monitored using image guidance to attain potentially differing iceball sizes as needed, ensuring adequate tumor coverage. Part (a) of FIG. 4 provides an axial view that illustrates a suitable placement of the six probes 100 in treating an irregularly shaped tumor. Each probe may produce about 2.5-cm diameter of visible ice (i.e. 0° C.) on ultrasound or x-ray computed tomography. Curves 404 denote a boundary of the visible 0° C. ice-line region. A boundary of cytotoxic, or lethal (i.e. less than about −40° C.), ice is denoted with curves 408, which is generally about 3-5 mm behind the leading edge of the visible ice.

The cryoprobes 100 may thus be placed to approximate the irregular contours of the tumor, with each probe being driven only to the extent needed to provide lethal coverage. The freeze length may be about 5-cm of lethal ice. After about a ten-minute freeze cycle, the ice reaches its maximum freeze intensity, as seen in the full-ice axial and sagittal images in parts (b) and (c) of FIG. 4, in which the contour of the −40° C. line covers all tumor margins. Neighboring normal tissue is thus spared by driving the probes 100 only to the extent required to provide thorough tumor coverage, effectively sculpting the ice.

Figure 5:
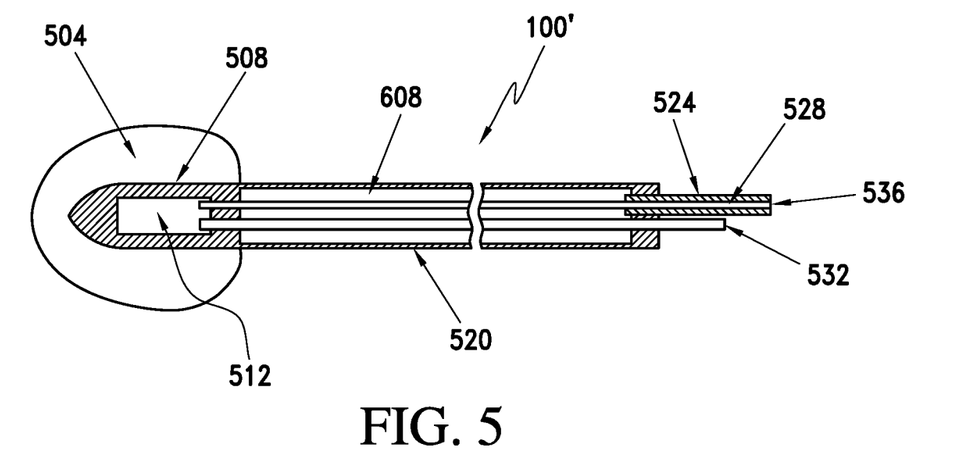
FIG. 5 is a schematic illustration of a cryoprobe in an embodiment of the invention using a liquid-nitrogen circulation cycle.

A liquid-based cryoprobe is illustrated for an alternative embodiment in FIG. 5. In this embodiment, the cryoprobe 100' uses a liquid nitrogen circulation cycle. Liquid nitrogen may be supplied to the cryoprobe at inlet 536 through inlet capillary 528, which is thermally insulated with insulation 524. The liquid flows to an evaporation and exchange zone 512 at the tip 508 of the probe 100' to produce an exterior freeze zone 504. An outlet capillary 532 provides a return flow path for the liquid nitrogen. The inlet and outlet capillaries are housed within a shield 520 that encapsulates an interior vacuum.

Figure 6:
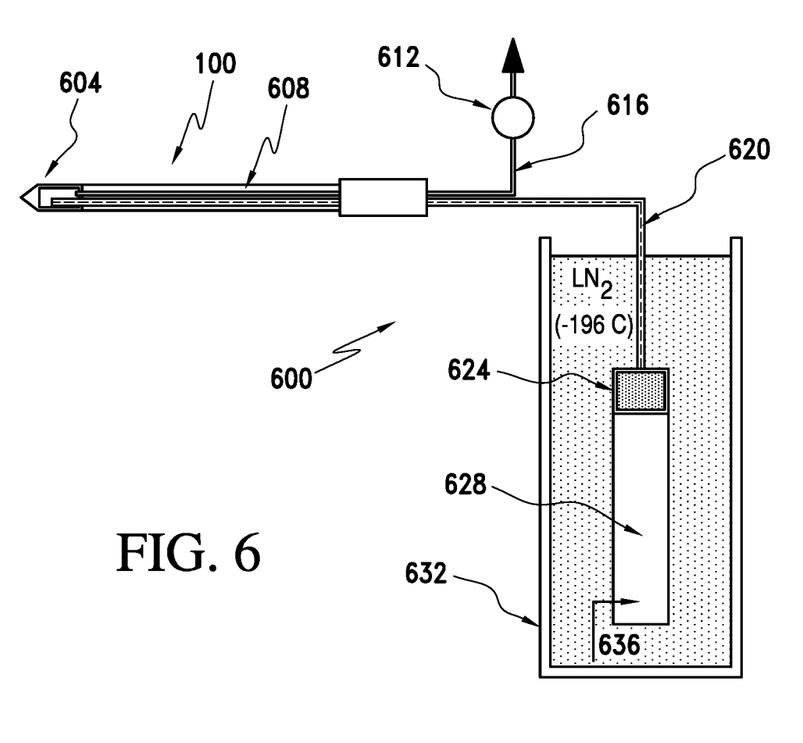
FIG. 6 provides a schematic view of a cryoprobe and simplified near-critical system according to an embodiment of the invention.

FIG. 6 provides a schematic view of a system 600 with which the cryoprobe 100 may be used in some embodiments. A simplified version of the cryoprobe is shown as comprising a probe tip 604 and a vacuum jacket 608, although the probe 100 will have additional features such as described above. The liquid nitrogen is held within a storage vessel 632 and is supplied through an inlet 636 to a compressor 628. A heat exchanger and pressure controller 624 acts to supply the liquid nitrogen to the probe 100 through a supply line 620 and to stabilize pressures within the probe 100. The supply line 620 may be disposed within a vacuum jacket between the heat exchanger/pressure controller and probe 100. Flow 616 is regulated at the output of the cryoprobe 100 with a flow controller 612, allowing gaseous nitrogen discharge. Further description of cryotherapy systems that may be used with the cryoprobe 100 are discussed in commonly assigned, concurrently filed U.S. patent application Ser. No. 10/757,769 entitled "CRYOTHERAPY SYSTEM," by Peter Littrup et al., now U.S. Pat. No. 7,083,612, the entire disclosure of which has been incorporated herein by reference.

Figure 7:
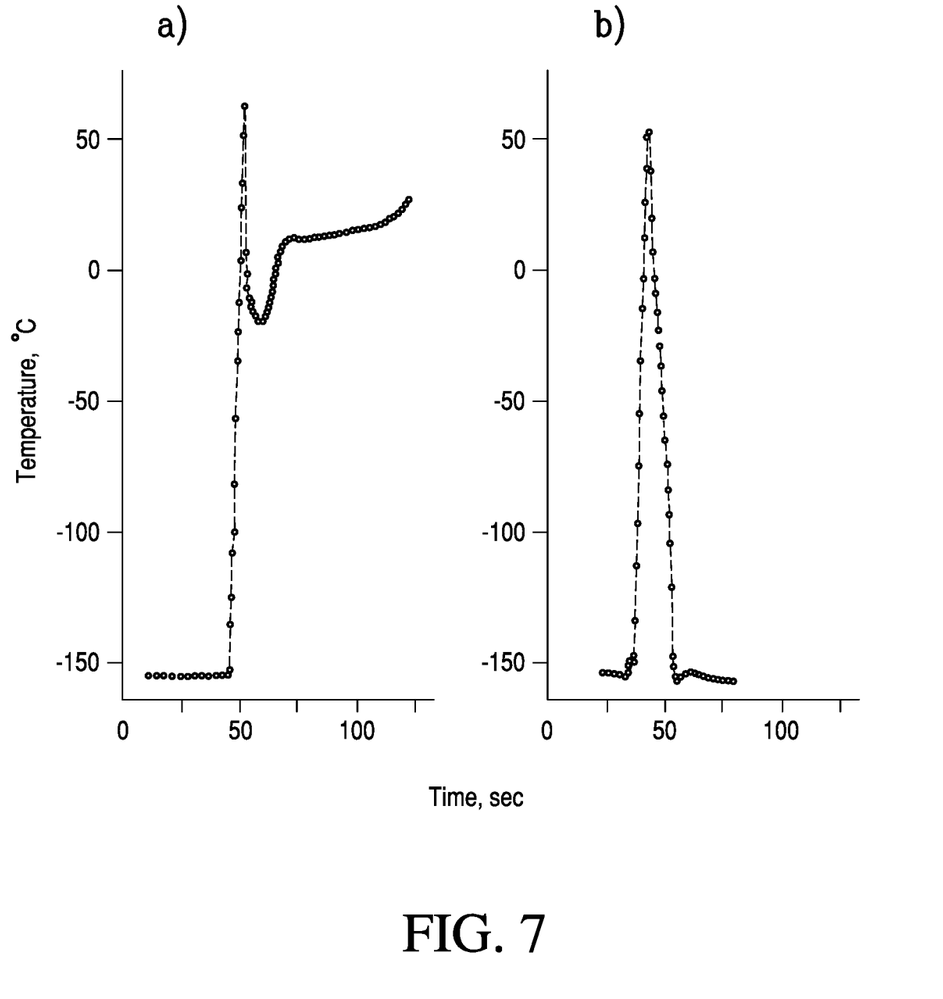
FIG. 7 displays experimental data illustrating certain properties of cryoprobes made in accordance with embodiments of the invention.

FIG. 7 provides data from experiments using the cryoprobe designs described above. The experimental data were taken with a 6.6 W heat load applied continuously to the tip of the probe, with the supply and return lines maintained within the vacuum-insulated shaft. Part (a) of the figure displays the tip temperature of the probe as a function of time during vapor lock recorded when the nitrogen pressure in the probe was 13 bar. At t=48 sec, the flow through the probe was momentarily stopped and then resumed after approximately 5 sec. As clearly seen, the heating of the probe's tip to approximately room temperature resulted in vapor lock, and the probe did not reachieve its deep freeze. The results for a similar procedure performed at 29 bar, i.e. near the critical pressure of 33.5 bar for nitrogen, are shown in part (b) of FIG. 7. A remarkably speedy recovery is evident from heating to about 50° C. to its freeze temperature of −153° C. In both cases, the flow rate through the probe was maintained on the level of about 10-15 STP L/sec. This demonstrates the advantage of operating near the critical point pressure to obtain reliable and rapid cooling power in the probe for all applications using rapid delivery of any liquid cryogens via a small tube, canula, needle, etc. We note that at the near-critical pressure of 29 bar, the time required to cool the probe tip under this heat load was exceptionally short (typically a few seconds), meeting the particular need for rapid freeze operations in cryosurgery. In part (c) of FIG. 7, the top plots display the pressure and the flow rate of the $LN_2$ in the probe, and the bottom plot displays the tip temperature of the probe. When the flow was cycled on and off momentarily at 13 bar (at time t=115 s), the probe vapor locked and did not reachieve its deep freeze temperature until the pressure was increased further to 22 bar at t=200 s. Even at this pressure, a momentary on and off cycle at t=250 s resulted in sluggishly slow cooling and an unacceptable base temperature of the probe until the pressure was increased to near 29 bar at t=325 s. At this pressure, very near the $LN_2$ critical pressure of 33.5 bar, the probe cycled rapidly between room temperature and 120 K (−150° C.) as the pressure was cycled. This further confirms the need for less than 2 mm to function at near-critical pressure for the initiation of a freeze, completely avoiding vapor lock.

Figure 8:
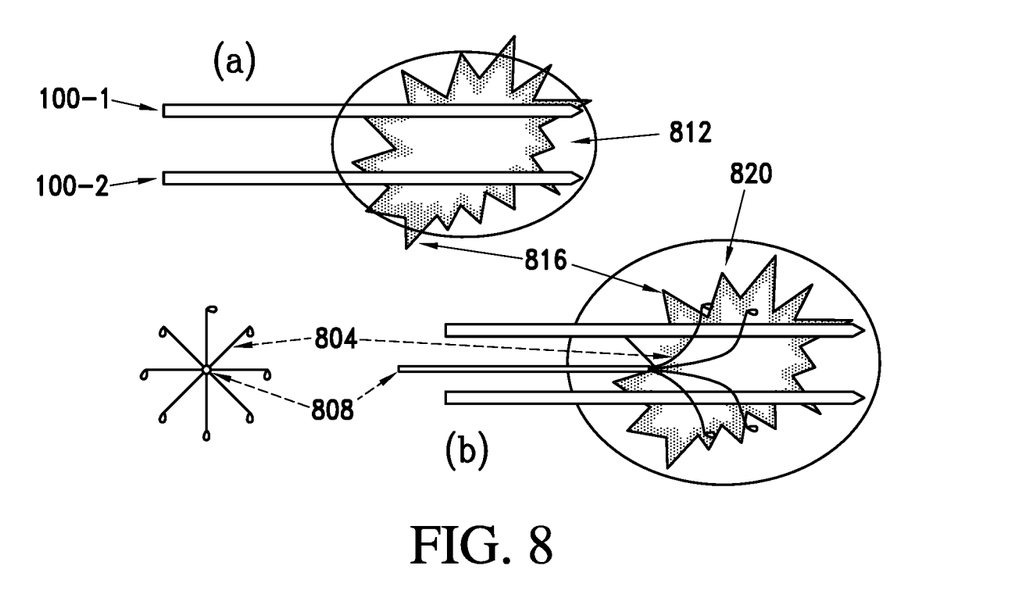
FIG. 8 provides an illustration of the use of cryoprobes within an irregular tumor.

In some embodiments, an injection-probe system, either within a separate probe or integrated into the vacuum jacketed space of the cryoprobe, may be used to improve ice distribution, an illustration of which is provided in FIG. 8. Part (a) of FIG. 8 shows two cryoprobes 100 within an irregular tumor 816 with ice 812 that fails to cover several margins of the tumor 816. Part (b) shows a separate injection probe system, with the left portion of the drawing showing a top view of the system and the right portion of the drawing showing a side view that illustrates the effect on the ice distribution 820. The separate injection probe system comprises a central probe 808 and a plurality of injection lines (i.e. ports 804) distributed radially and/or axially about the central probe 808. The use of the separate injection probe system easily allows the ice to propagate further, covering the entire tumor.

A variety of different fluid combinations may be delivered by the injection probe system. For example, macroaggregated albubin may be provided to decrease subsequent fluid extravasation by creating an interstitial gel effect, followed by a ~7% solution of NaCl containing 1:100,000 epiphrine, causing a significant decrease in heat sink effects through vascular constriction, as well as more thorough cytotoxicity via greater osmotic shock. Other fluids containing, but not limited to, chemotherapeutic or radiotherapeutic agents may also be delivered in a similar fashion. Also, the injection tines delivering the fluid do not need to be contained within a separate injection probe system, but could be alternatively be configured within the shaft of the cryoprobe. The resulting increase in cryoprobe diameter may be functionally offset by having a single insertion device for both injection and cryotherapy.

A number of features and alternative embodiments to the specific embodiments described above, in both gas and liquid-based embodiments, are noted below.

1. Image Artifact Reduction and Enhancement of Freeze Probe Tissue Kill Rate with Electrical Ablation The main shaft of the probe may comprise a metallic, ceramic, or composite material and is vacuum jacketed from the inner heat exchanger to assure that the outer shaft remains at ambient temperature. Composite materials are favored for their low cost, strength, and low density. Due to the initial success of percutaneous cryotherapy by CT guidance, one embodiment of the invention utilizes the lowest density outer sleeve to avoid beam hardening artifact, frequently seen in CT images. Since multiple probes create even further beam hardening, any significant reduction in density produces much greater overall improvement in image quality during treatment monitoring. The titanium sleeves are given as an example of a non-magnetic metal that is already used for MRI-compatible probes.

The shaft of the cryoprobes may be made of an electrical insulating material, such as a ceramic or a composite material. This permits the electrically conducting probe to be used as an electrode in an electrical ablation application. Once multiple probes have been placed within the tumor tissue, an electrical current may be forced to flow from one probe tip to another. This may be driven to cause enough interposed tissue heating to generate some coagulation, thus reducing the blood flow through the region primarily between the probe tips. However, this may elicit pain despite making the tissue much easier to freeze. The heating function may then be better utilized after an initial quick freeze and then cycled on and off. Once the freeze has resulted in an iceball between the probe tips, another electrical current may be passed between the probe tips to destroy tissue at the periphery of the freeze zone, and to further attenuate blood flow at the periphery of the tumor. In this application, once an iceball exists between the probe tips, then the frozen tissue is a much worse electrical conductor than the tissue surrounding the iceball. Hence, the electrical current will flow from one probe tip to the other, primarily in the periphery of the tumor around the ice margin, helping destroy tissue and blood flow in this peripheral region. One electrical ablation/cryogenic ablation sequence may thus include alternating freeze periods and electrical ablation periods. This sequence may be determined by the physician during the tumor ablation procedure, based primarily on the efficacy of generating the largest feasible ablation zone as determined by near real time imaging of the tissue being ablated.

2. Vacuum Jacket Utilization

One purpose of the vacuum jacket is to assure that tissue between the point of insertion and the region to be frozen is not damaged. However, it can also serve as a viable space to transmit the below noted additional probe options. This includes, but is not limited to, temperature sensors, capillary channels for combined injections, position sensor technology and electrical stimulatory leads. Most current gas-based probes have vacuum jacketing but no liquid-based cryoprobes are currently in use with vacuum jacketing to enclose a side-by-side configuration of supply and return $LN_2$ lines.

3. Reduced Flow Impedance

For gas-based embodiments, the counterflow heat exchanger between the JT valve and the neck of the instrument may be chosen in order to achieve the necessary heat exchange between the incoming and outgoing gas at the lowest possible gas flow impedance. The outgoing and incoming gas lines transition into their laminar flow regime at the first possible opportunity in the counterflow design in order to avoid the unnecessary pressure drops associated with standard turbulent flow regimes in current cryotherapy probes and their associated support tubing. The laminar flow concept permits the engineering of the smallest gap possible without passing into the turbulent flow regime, assuring the best cryogenic functionality in the smallest possible probe diameter. For example, at low flow rates, initial calculations for argon gas suggest that it would be desirable to have an approximately 0.010" gap between the inner high pressure line and the outer low pressure return line. Hence the outer diameter of the return tube may, for example, be 0.080" (2 mm), with an ID of 0.070". The high pressure supply line, running co-axially, can, for example, have an OD of 0.060" and an ID of 0.050". This plan will result in laminar flow in both lines, producing a low flow impedance and subsequently less compressor requirements. Sufficient design flexibility exists in this design to change dimensions as may be desirable to accomplish better performance with other gases.

For liquid-based embodiments like the one described in connection with FIG. 5, one technique for avoidance of flow disruption in the form of vapor-lock for liquid cryogens, such as $LN_2$, is compression of the liquid to its near-critical phase, as previously noted. As the data in FIGS. 1 and 7 suggested, a higher pressure near-critical fluid phase for $LN_2$ could be utilized for a "stick" mode. The subsequent "freeze" mode can then utilize lower pressure and cooler fluid temperatures for improved cooling capacity. Similar to the above low impedance for gas-based systems, elimination of vapor-lock in probes using $LN_2$ now permits very small (i.e., <1 mm) probe diameters, as well as probes <2 mm which have similar, or greater, cooling capacity than either current 2.4 mm JT probes using argon or prior 3 mm $LN_2$ probes. The supply return line ID ratio for our near-critical $LN_2$ embodiment should be fairly stable at 0.6 (⅗) in the interval of all practical flow rates, regardless whether we employ a ~1 mm or ~2 mm probe design. Notably, efficient $LN_2$ utilization for our near-critical $LN_2$ embodiment allows an open or closed-loop $LN_2$ storage system. Our near-critical approach allows a self-contained unit for both large applications (~2 mm), as well as a compact, convenient system for nerve applications (~1 mm), or other non-medical uses requiring only short freeze bursts on the order of seconds, rather than several minutes. Our current estimates of $LN_2$ utilization is 1.8 liters of $LN_2$ should be sufficient to power one ~2 mm probe at ~20 Watts continuous cooling power for at least sixty minutes. This appears scalable, such that a single charge of 5-10 gallons of $LN_2$ would be adequate for 3 typical prostate cases without refilling (i.e., assuming 6 probes, ~1.5-2.0 mm diameter, and 2 cycles of 20 minute freezes per case). An embodiment of the Near Critical $LN_2$ system design (FIG. 6) may contain a flow controller at the discharge port that will also consist of the main impedance in the system. This permits the probe pressure to remain very close to the near critical pressure produced within the supply dewar insert. More detailed system configurations are described in U.S. patent application Ser. No. 10/757,769, entitled "CRYOTHERAPY SYSTEM," by Peter Littrup et al., which has been incorporated by reference.

4. Heat-Exchanger Modifications (Gas-Based)

In some embodiments, strips of high thermal conductivity material, such as copper foil, are soldered to the inner (high pressure) supply tube and extend out radially to permit good heat exchange with the cold, low-pressure return gas. This differs from the spirally wrapped tube along the inner supply tube that is employed in some other designs. This construction ensures the improved heat exchange over the length of the counterflow heat exchanger, which is set by the medical application. In one embodiment, this inner tube is made of high thermal conductivity material, such as copper. The counterflow heat exchanger may also be thermally isolated from the surrounding tissue using a vacuum sheath, as shown in FIG. 2. This provides greater efficiency and refrigeration power in the freeze zone tip, resulting in faster and more efficient tumor freeze. It is possible to accomplish the same iceball sculpting of shape without repositioning a vacuum sheath through independent flow control through each JT from the room temperature controller.

Both the liquid and gas systems may also incorporate an evacuated annular sheath that surrounds part or all of the freezing portion of the probe. This vacuum sheath will run co-axially with the body of the cryoprobe, and may be extended or retracted by the physician performing the cryotherapy or cryosurgery. Such a configuration permits the physician to change the length of the active freeze zone of the probe to affect the necessary change in the freeze zone of the surrounding tissue based upon near real-time information obtained from various imaging modalities from radiology. Another possible shape of the ice surrounding both gas and liquid-based freezing could relate to the relative thickness and/or conductivity of the probe tip material interposed between the tissue and expansion chamber.

5. Computer-Controlled Separate JT Ports

Figure 1:
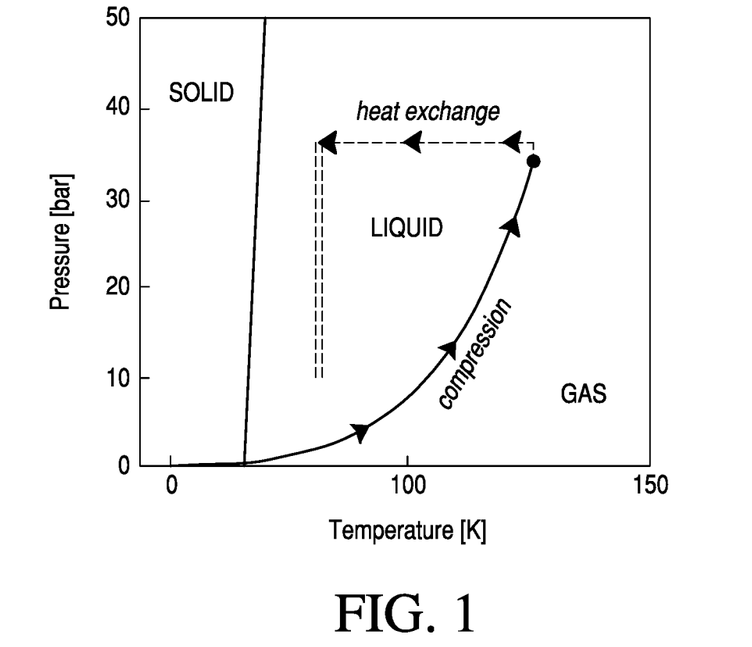
FIG. 1 is a phase diagram illustrating the phase structure of a liquid like $LN_2$.

FIG. 4 demonstrates the overall clinical concepts involved in ablating any tumor by any interstitial source. The primary concept is to visualize the tumor margin and treatment margin. In this regard, cryotherapy holds a distinct advantage over the difficult to visualize heat-based treatment margins. Separate computer controlled ports are thus only an issue for each cryotherapy probe needed to sculpt the lethal freeze margin to the tumor margin (FIG. 4). The region downstream from the JT valve may be constructed from a metal with good thermal conductivity, such as gold plated copper. This region may taper to a sharp tip to aid in insertion through tissue, or retain a blunt tip for use with an insertion kit. The length of this region is customized to the extent of the tissue to be frozen. Typically this length is set at approximately 80% of the linear extent of the intended freeze region. Each cryoprobe's freeze zone, total shaft length, and diameter are set by the medical plan for the surgery, and each probe may be custom tailored to the planned cryosurgery. Most probes will have only one JT port, as shown in FIG. 1, but certain custom applications may have multiple independently controlled JT ports, and hence multiple freeze regions, along the length of the instrument. In addition, the laminar flow concept allows for greater efficiency of gas utilization when double JT ports are simply set in the end of the probe for the largest spherical ice ball. (Typical dimensions for a single JT port cryoprobe for use on a 3 cm tumor would be: 2.0 mm diameter, 120 mm shaft length with a 4 mm long active freeze region. Typical dimensions for a cryoprobe for use on a small nerve would be 1.0 mm diameter shaft of 100 mm total length, including a 1.0 cm active freeze zone. All of these dimensions may be optimized for the intended freeze region using a thermal model of the tissue and good engineering design.)

In one embodiment that uses near-critical liquid nitrogen probes, only one expansion chamber/cooling tip is used per probe. However, a near-critical $LN_2$ probe having separate computer control may alternatively be used in which 2-3 small (e.g. ~1 mm) separate freezing probes are contained within a larger probe/introducer sheath (i.e., ~2-3 mm). The small inner probes could then be deployed into an area (e.g., tumor), creating a larger faster freeze than a single larger (~3 mm) probe. The relative merits to this insertion option over simply placing 2-3 ~1 mm separate probes could relate to a difficult probe trajectory (i.e., between ribs, or avoiding other interposed tissue). Therefore, separate computer control of freeze zones could be conceived as either contained within one probe (i.e., for whatever insertion benefit) or within separate probes to allow better overall sculpting of the total freeze region.

6. Probe Integration and Construction Options

In some embodiments, these cryoprobes may have the necessary external interface structure at the neck of the shaft to be driven by robotic positioning systems that may be used to position the probes precisely within the freeze region with physician-controlled guidance with real-time imagery, such as CT, MRI or ultrasound. Most American institutions require disposable probes for procedures coming in contact with internal body fluids (i.e. blood, organ tissues) and accordingly, in some embodiments, the composite materials, probe junction handles and tubing are selected for minimal cost. However, in other embodiments, cryoprobes are intended to survive autoclave temperatures without damage and re-used many times. Following the medical procedure, probes may also be returned for a recycling credit to reduce medical waste.

7. Spatial Localization Mechanisms

Each cryoprobe may contain separate device(s) to provide better integration with three-dimensional imaging localization. This may take the form of a radiofrequency device which can be interrogated from the surface to determine its internal localization. Localization of each cryoprobe tip can then be compared with the predetermined optimal position (i.e., on the preoperative planning session) for adjustments and control of each cryoprobe's freeze intensity and/or duration. Any other internal localization mechanism other than radiofrequency may be used in alternative embodiments, such as ultrasound localization of the "whistling" produced by the JT port, or possibly the liquid end chamber. For example, in one embodiment this takes the form of cryoprobe angulation assessment of its final position within the patient in comparison with the preoperative plan.

8. Electrical Thaw, Temperature Measurement, and Nerve Stimulation

One embodiment of the cryoprobes uses a length of electrically insulated resistive wire (various compositions of this resistive metal (alloy or pure) may be used) within the freeze region of the cryoprobe for three potential functions. First, the resistance of this wire is measured using a four-wire technique, and this resistance is used to determine the temperature of the freeze tip. Second, these wires can be used to heat the freeze section of the probe. Once the freeze process is complete, the flow of gas is stopped through the cryoprobe and a much larger electrical current is placed through the resistive wire to create a rapid thaw of the frozen tissue near the probe so that the probe may then be easily extracted. A second 'thaw gas' becomes unnecessary, thus providing more room in the probes and simplifying the system to a single gas regimen. Or, a modification could be assumed where helium gas or low-pressure, heated nitrogen gas is used in an open system once the closed-loop freeze is complete. Alternatively, the more generalized heating of the probe tip by a second gas (i.e. helium) could still be done. Third, these wires can also provide the necessary nerve stimulation for sensory and motor testing, provided that the tip of the probe is electrically conducting and that the shaft of the probe is electrically insulating. Such a configuration would provide stimulation from a wire used on one side of the heater/thermometer resistive wire within the probe, with the return path for the electrical stimulation being the patient's body. In another configuration separate, dedicated wire pairs may be used within the probe for nerve stimulation, or sensory or motor stimulation. These electrical stimulation wires, and/or wires for electrical heaters and/or gas flow lines for thaw gasses, may be used either in conjunction with the cryotherapy probes, or in separate probes developed for this purpose.

Figure 9:
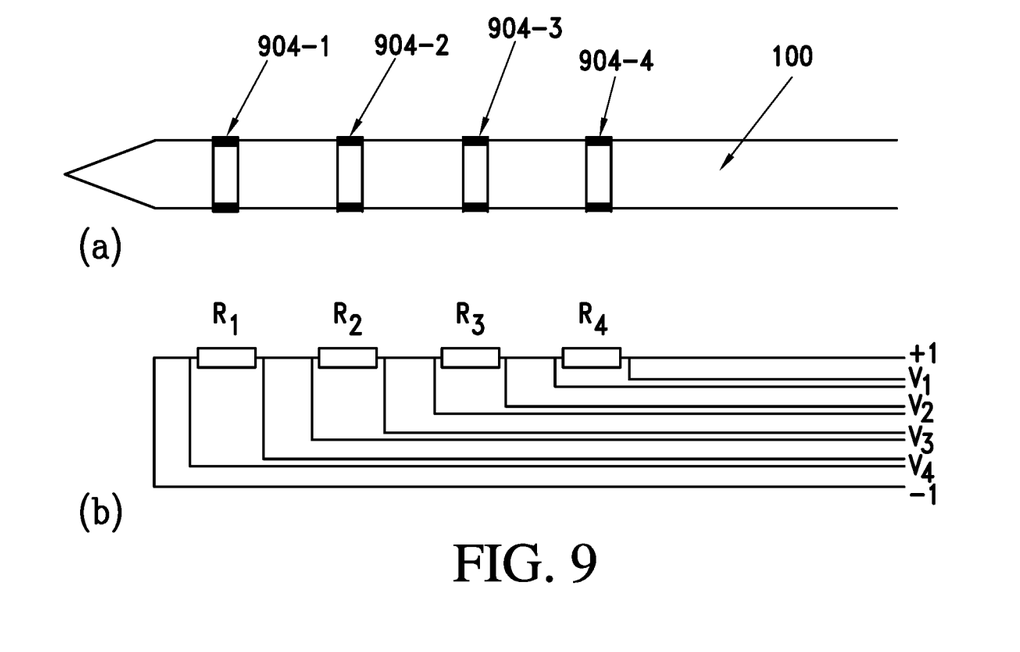
FIG. 9 provides an illustration of an embodiment for the cryoprobe having a plurality of temperature-sensitive resistors.

Embodiments of the invention thus permit accurate, rapid thermometry of the cryoprobe tip in very small geometries while reducing the cost of this thermometry to well below the current cost of thermocouple measurement systems in use on large cryoprobe probes in use today. Therefore, as shown in part (a) of FIG. 9, separate thin probe (e.g., 21 gauge) resistance thermometers 904 may be constructed in a linear ray along the probe 100 to provide more than two measurement points. These embodiments use very thin copper wire, typically AWG 40 or smaller, to replace the thermocouple. Part (a) of FIG. 9 shows outer segments of wire wrapping for one embodiment of either a separate probe or a cryoprobe itself, with a thin outer coating (e.g. made of TEFLON®) provides for smooth, non-stick insertion, yet not buffer rapid temperature response. The electrical resistivity of this copper wire varies with temperature, varying by approximately a factor of five between room temperature and 77 K. This resistivity of the copper wire is calibrated against temperature over this range so that measurements of this electrical resistivity may be converted to temperature for use in the operation of these cryoprobes. Part (b) of FIG. 9 shows an electrical diagram illustrating the electrical character of the physical arrangement shown in part (a). The variation of the electrical resistivity of copper with temperature is linear and very predictable over this range, so the conversion of the measured resistivity to temperature is easily achieved in the associated readout software that supports this new method of thermometry. Two calibration points, one at room temperature (300 K) and one at $LN_2$ temperature under one atmosphere of pressure (77.3 K) are adequate to calibrate this method of thermometry over its full range.

One specific such embodiment uses about ten turns of a very small diameter wire on a post that is part of the cryoprobe's tip. A digital to analog converter (DAC), controlled by the measurement computer, is used to supply the measurement current I through the wire. All of the probe thermometers may utilize the same DAC current supply. Each wire wrap on each of the probes has two additional leads bonded one each to each end of the current carrying wire wrapped around the cryoprobe tip (which temperature is to be measured) that lead to a dedicated instrumentation amplifier and then to an analog to digital converter ('digitizer, or ADC) to convert the voltage drop along the current carrying wire to a digital readout, which then can be displayed on the computer to the operator, and/or used by the computer in an expert system that automatically controls the cooling of the probe in response, in part, to this temperature indication, and to other indications that come from imaging systems.

The current through each of the wires wrapped around the posts within each cryoprobe will be held constant as the ADC dedicated to each wrapped wire measures the 'forward' voltage $V_+$. The current is then reversed in direction by setting a voltage of the same magnitude, but of opposite polarity, under computer control, and then the 'reverse' potential drop $V_-$ is measured. The actual voltage drop across the wrapped wire is then $V=(V_+-V_-)/2$, while the thermal electromotive force differential associated with the measurement leads is $V_T=(V_++V_-)/2$. This method of current reversal is used to eliminate errors associated with differential lead thermals in the measurement of the actual voltage drop across the wrapped wire. The resistance of the wrapped wire $R=V/I$, and this resistance is converted to temperature using the known variation of the copper resistance R with temperature T, which over this range of temperature is, to within adequate accuracy, a linear relationship. In practice, this current reversal, punctuated by voltage measurements in each current direction, occur frequently and periodically, with a typical period of about 10 current reversals ('cycles') per second. The controlling computer then calculates the wire resistance R as described above during each cycle of the current reversal, and uses the calibration function to convert this resistance to temperature.

The wire used in this technique is typically very small in diameter (typically AWG 40 or AWG 38; note that AWG 38 copper wire was used to make the measurements displayed on the prototype probe reported in the figures within this application). This small wire may be easily wrapped around a post attached to the probe tip and within the cryoprobe's vacuum space even on very small probes, without requiring special fabrication techniques. In addition, small diameter insulated copper wire is readily available commercially, and often called 'magnet wire'. The cost of the wire used in each cryoprobe is typically much less than one cent, and literally a thousand times less expensive than a conventional thermocouple. This leads to a much lower cost to develop each probe, reducing the cost considerably for the disposable probes used in most medical procedures.

While this example has specifically mentioned the use of small diameter insulated copper wire, any other wire (aluminum, silver, gold, platinum, or alloy) with a substantial temperature coefficient may be used in the same way. The variation of the resistance of whatever wire material is used may be determined by direct calibration during the development of the class of cryoprobes and associated support systems, and this calibration, once determined in this manner, may be used in the operation of all probes subsequently made of this wire material. As evident to those skilled in the art, this same measurement technique may be applied to wire attached in any manner that provides adequate thermal contact to the object which temperature is to be measured, as suggested in the discussion of FIG. 9.

This method of thermometry provides an additional advantage when applied to cryoprobes for percutaneous cryotherapy. The current through the wires anchored to the cryoprobe tips is controlled by the computer through its DAC, as discussed above. During the 'thaw' or the 'un-stick' process the current through these wires may be easily increased to much higher levels, producing direct ohmic heating to the probe tips of many watts (typically 30 W). This provides the immediate heat necessary to accomplish the thaw or un-stick without the added system complexity of having to switch to a different thaw gas in the flow channel, such as helium gas. This also permits much more rapid freeze/thaw switch over, which may be advantageous in certain medical procedures. The upper target temperature for ohmic heating may be limited to <45° C. to avoid any unwanted tissue damage. Alternatively, the puncture tract of the probe could be cauterized at higher temperatures to ablate any bleeding tendency as needed.

9. Micro-Injection Lines

In one cryoprobe embodiment, micro-injection ports are provided along the distal extent of the probe. These cryoprobes may be particularly effective for their use with kidney tumors, which have higher blood flow and risk of hemorrhage. However, as greater understanding of cryo-sensitizers and augmented cryo-biology develops, injected substances could extend beyond the current suggestion of vasoconstrictive cocktails [e.g., macro-aggregated albumin (MAA) followed by hypertonic saline with epinephrine] to include any variety of chemotherapeutic, radiotherapeutic, or immunotherapeutic substances delivered by the same cryoprobe. The separate multiprong injection system described in connection with FIG. 8 above may also be used. These micro-injection lines may run through the evacuated space of the cryotherapy probes, or separate probes may be developed for this purpose.

10. Nerve Stimulation and Probe Modifications for Pain Ablations

Pain management currently uses RF probes that are ~20 gauge in diameter (i.e., <1 mm outer diameter). In an embodiment, a cryoprobe having minimal freeze capacity is provided using the probe design, such that its overall diameter is ≤1 mm. The maximal ice ball diameter might only be 3-6 mm, depending upon the nerve location. For example, posterior facet joints of the spine, as well as peripheral nerves, would only require an ice ball diameter of 3-4 mm. Ablations of even sympathetic ganglions, or stellate ganglions, would only require ice ball diameters of no more than 5-6 mm. The previously noted electrical wires may thus serve a stimulatory role for confirmation of accurate probe tip location both motor and a sensory nerve testing. For example, sensory nerves are frequently stimulated at 50 hertz with 1 mV potential difference from surrounding tissue, whereas motor nerves are stimulated at 2 hertz with 3 mV potential difference from the surrounding tissue. In addition, the micro-injection ports near the probe tip may serve to instill local anesthetic down to the target level.

11. JT Port Considerations

The dimensions of the JT port shown in FIG. 3 are provided to match the dimensions of the cryoprobe, which are set by the intended medical application. The JT ports contain a high yield strength wire, made for example from hardened steel or a niobium-titanium alloy, that extends about 3-5 capillary diameters into the supply tube. The length of the supply tube over this region is made from a strong, high yield strength allow such as steel tubing alloy and joined to the gas supply tubing. This wire vibrates due to the hydrodynamic forces on the wire exerted by the exceptionally high flow speeds of the gas near this JT port opening. Such mechanical vibrations of this hard wire break up frozen impurities that threaten otherwise to block the JT port. This innovation permits the use of very small JT ports without the risk of impurity freeze-up, and novel multicomponent mixtures to be used as the gas in the closed cycle system without risk of fouling the JT due to selective freezing of the closed cycle gas components, or impurities within the closed cycle gas system, at the JT port. This same concept may be used in all orifices that support high Reynolds' Number flow patterns in order to prevent them from clogging or fouling under combustion or other chemical reactions.

Impure natural gas is often purified using a JT port expansion process and counterflow heat exchanger. $CO_2$ impurities are frozen out along the heat exchanger, often in dedicated traps and/or sumps. The combustible hydrocarbons are liquefied at the JT port expansion chamber, while the $N_2$ impurities remain within its gaseous phase and are blown off. The liquid combustible hydrocarbons are then evaporated on return to ambient pressure before delivering to the natural gas pipeline or storage. Alternatively, the liquefied combustible natural gas may be extracted in its liquid state for use in liquefied natural gas-fueled vehicles and engines. Embodiments of the JT port described herein may be applied to for JT ports in natural gas purification devices and liquefaction systems to avoid fouling or clogging. Other such examples include engine fuel injectors, chemical spray nozzles, and water jets that may become fouled by hard water or seawater deposits. Such further applications are also within the intended scope of the invention.

12. Connector Handle

As previously described, each cryoprobe neck may comprise two gas lines. One line is a high pressure supply from the flow controller system and the other is a low-pressure return line to the supporting engineered system. The pressure lines connect to the flow control system using hermetic quick connectors so that they may be connected and disconnected readily without contamination to the closed cycle gas system. In one embodiment, an appropriate filter is also placed within the probe or system to avoid possible contaminants from the reconnection process. A plurality of wires, such as four wires in a specific embodiment, feed through this neck assembly and go to the thermometer/heater/electrostimulation control units. For the micro-injection embodiment shown in FIG. 8, four capillary tubes may also run through the neck assembly (as well as through the vacuum sheath as needed) in conjunction with the thermometer/heater wires such that they can remain unclogged (i.e., unfrozen) when probes may be placed to "stick."

13. Alterative Cooling Processes

As an alternative cooling process for the cryoprobe, the cryoprobe may be cooled by a pulse tube expansion engine, or any other such driver that subsequently cools the cold end of the cryoprobe through thermoacoustic oscillations. In this manifestation the cryoprobe will become the tuned cold section of the pulse tube refrigerator. The drive engine for the pulse tube refrigerator will disconnect from the cryoprobe through a hermetic quick connector at room temperature, and each cryoprobe may have its own room temperature drive engine that is specifically tuned to the cryoprobe. One advantage of this method is the ability to shift from freezing to thaw heating merely by changing the acoustic phase of the drive at room temperature, using a simple acoustic phase shifter. Helium may be used as the working gas in both the freezing and thawing. Other aspects of the cryoprobe design described herein remain the same, except in this manifestation no inner supply tube or associated heat exchanger is required. Wires for the resistive thermometer readout, and tubes for the micro-injection lines described above, may feed through into the cryoprobe between the base of the pulse tube engine on the probe side of the hermetic quick connector. In this manifestation the pulse tube engine may weigh about ten pounds, and may be mounted on an adjustable support structure over the patient.

Other methods and variations of cryoprobe cooling may be considered to be technical variations on these designs. These cooling modalities may include isentropic expansion cooling of a gas, flow liquid state cryogen cooling, all gas expansion cycle cooling modalities, and electrical junction cooling (Peltier Effect Cryocooling), and all combinations of such cooling modalities to create the iceball.

The methods of the present invention may be embodied in a computer-readable storage medium having a computer-readable program embodied therein for directing operation of a cryotherapy system such as described above. The computer-readable program includes instructions for operating the cryotherapy system in accordance with the embodiments described above.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method of cooling a material comprising the steps of:
   providing a cryotherapy instrument;
   positioning a portion of the cryotherapy instrument adjacent the material to be cooled;
   circulating a cryogenic fluid through the cryotherapy instrument under physical conditions near a critical point of a liquid-vapor system for the cryogenic fluid, wherein the critical point defines a point in a phase diagram of the liquid-vapor system where molar volumes are substantially equivalent for liquid and gas, whereby vapor lock associated with cooling of the cryotherapy instrument is avoided.

2. The method of claim 1, wherein the step of circulating the cryogenic fluid comprises circulating the cryogenic fluid for an initial period of time.

3. The method of claim 2, further comprising the step of maintaining the pressure of the cryogenic fluid during the initial period at a near critical pressure of the cryogenic fluid.

4. The method of claim 3, wherein the step of circulating the cryogenic fluid comprises circulating cryogenic fluid for a freeze period subsequent to the initial period.

5. The method of claim 4, wherein the pressure of the cryogenic fluid during the freeze period is less than the pressure of the cryogenic fluid during the initial period.

6. The method of claim 1, wherein the cryotherapy instrument comprises a shaft having a distal section with a closed distal end and an active freeze region in the distal section.

7. The method of claim 6, wherein the material to be cooled is human tissue.

8. The method of claim 7, wherein the shaft comprises a metal material adapted for percutaneous insertion into the human tissue.

9. The method of claim 6, wherein a length of the active freeze region is approximately 1 cm.

10. The method of claim 7, wherein the human tissue is a tumor.

11. The method of claim 1, wherein the circulating step comprises circulating liquid nitrogen at a pressure of about 33.5 atm.

12. The method of claim 1, wherein the circulating step comprises circulating the cryogenic fluid through an inlet tube, an outlet tube, and a hollow cavity of the cryotherapy instrument.

* * * * *